US00PP35186P2

(12) United States Plant Patent
Beers

(10) Patent No.: US PP35,186 P2
(45) Date of Patent: May 23, 2023

(54) ***GERBERA* PLANT NAMED 'HILFHOTSPR'**

(50) Latin Name: *Gerbera hybrida*
Varietal Denomination: HILFHOTSPR

(71) Applicant: HilverdaFlorist B.V., De Kwakel (NL)

(72) Inventor: Martin Beers, Hoofddorp (NL)

(73) Assignee: HilverdaFlorist B.V., De Kwakel (NL)

( * ) Notice: Subject to any disclaimer, the term of this patent is extended or adjusted under 35 U.S.C. 154(b) by 0 days.

(21) Appl. No.: 17/947,154

(22) Filed: Sep. 18, 2022

(51) Int. Cl.
*A01H 5/02* (2018.01)
*A01H 6/14* (2018.01)

(52) U.S. Cl.
USPC ..... Plt./357
CPC ..... *A01H 6/1456* (2018.05)

(58) Field of Classification Search
USPC ..... Plt./357
CPC ..... A01H 6/1456
See application file for complete search history.

*Primary Examiner* — Anne Marie Grunberg
(74) *Attorney, Agent, or Firm* — C. Anne Whealy

(57) ABSTRACT

A new and distinct cultivar of *Gerbera* plant named 'HILFHOTSPR', characterized by its compact, broadly upright and uniformly mounding plant habit; moderately vigorous to vigorous growth habit; dense and bushy appearance; numerous large inflorescences with bright purplish red-colored ray florets with white-colored apices; upright and moderately strong peduncles; good garden performance and relative tolerance to low temperatures.

2 Drawing Sheets

Figure 1:
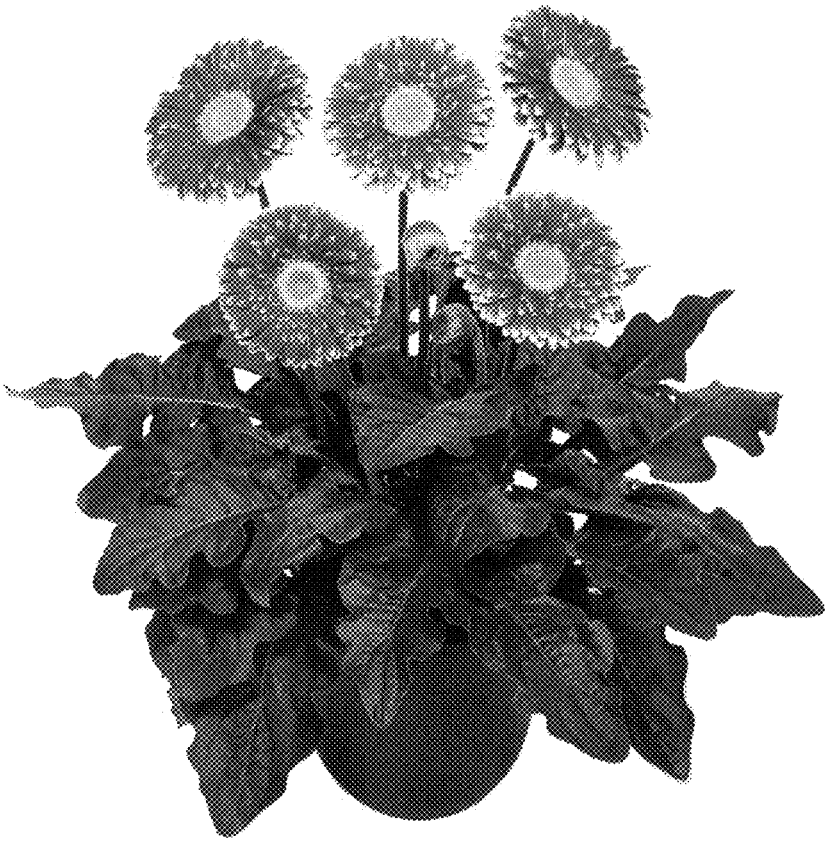

Botanical designation: *Gerbera hybrida.*
Cultivar denomination: 'HILFHOTSPR'.

BACKGROUND OF THE INVENTION

The present invention relates to a new and distinct cultivar of *Gerbera* plant, botanically known as *Gerbera hybrida* and hereinafter referred to by the cultivar name 'HILFHOTSPR'.

The new *Gerbera* plant is a product of a planned breeding program conducted by the Inventor in De Kwakel, The Netherlands. The objective of the breeding program is to create new compact garden *Gerbera* plants with numerous attractive inflorescences, resistance to low temperatures and good garden performance.

The new *Gerbera* plant originated from a cross-pollination during the spring of 2015 of a proprietary selection of *Gerbera hybrida* identified as code number 1679, not patented, as the female, or seed, parent with a proprietary selection of *Gerbera hybrida* identified as code number 1680, not patented, as the male, or pollen, parent. The new *Gerbera* plant was discovered and selected as a single flowering plant from within the progeny of the stated cross-pollination in a controlled greenhouse environment in De Kwakel, The Netherlands during the summer of 2016.

Asexual reproduction of the new *Gerbera* plant by vegetative terminal cuttings and in vitro meristem culture since the autumn of 2016 in De Kwakel, The Netherlands, has shown that the unique features of this new *Gerbera* plant are stable and reproduced true to type in successive generations of asexual reproduction.

SUMMARY OF THE INVENTION

Plants of the new *Gerbera* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'HILFHOTSPR'. These characteristics in combination distinguish 'HILFHOTSPR' as a new and distinct *Gerbera* plant:

1. Compact, broadly upright and uniformly mounding plant habit.
2. Moderately vigorous to vigorous growth habit.
3. Dense and bushy appearance.
4. Numerous large inflorescences with bright purplish red-colored ray florets with white-colored apices.
5. Upright and moderately strong peduncles.
6. Good garden performance and relative tolerance to low temperatures.

Plants of the new *Gerbera* differ primarily from plants of the female parent selection in the following characteristics:

1. Plants of the new *Gerbera* have larger inflorescences and with larger ray florets than plants of the female parent selection.
2. Plants of the new *Gerbera* have bright purplish red-colored ray florets whereas plants of the female parent selection have white-colored ray florets.

Plants of the new *Gerbera* differ primarily from plants of the male parent selection in the following characteristics:

1. Plants of the new *Gerbera* have shorter and narrower leaves than plants of the male parent selection.
2. Plants of the new *Gerbera* have lighter purplish red-colored ray florets than plants of the male parent selection.

Plants of the new *Gerbera* can be compared to plants of the *Gerbera hybrida* 'GLOLIP21AA', disclosed in U.S. Plant patent application Ser. No. 17/747,718. In side-by-side comparisons, plants of the new *Gerbera* differ from plants of 'GLOLIP21AA' in the following characteristics:

1. Plants of the new *Gerbera* have longer leaves than plants of 'GLOLIP21AA'.
2. Plants of the new *Gerbera* have slightly larger inflorescences than plants of 'GLOLIP21AA'.
3 Ray florets of plants of the new *Gerbera* are bright purplish red in color whereas ray florets of plants of 'GLOLIP21AA' are pink in color.
4. Plants of the new *Gerbera* have longer and thicker peduncles than plants of 'GLOLIP21AA'.

BRIEF DESCRIPTION OF THE PHOTOGRAPHS

The accompanying photographs illustrate the overall appearance of the new *Gerbera* plant showing the colors as true as it is reasonably possible to obtain in colored reproductions of this type. Colors in the photographs may differ slightly from the color values cited in the detailed botanical description which accurately describe the colors of the new *Gerbera* plant.

The photograph on the first sheet (FIG. 1) is a side perspective view of a typical flowering plant of 'HILFHOTSPR' grown in a container.

Figure 2:
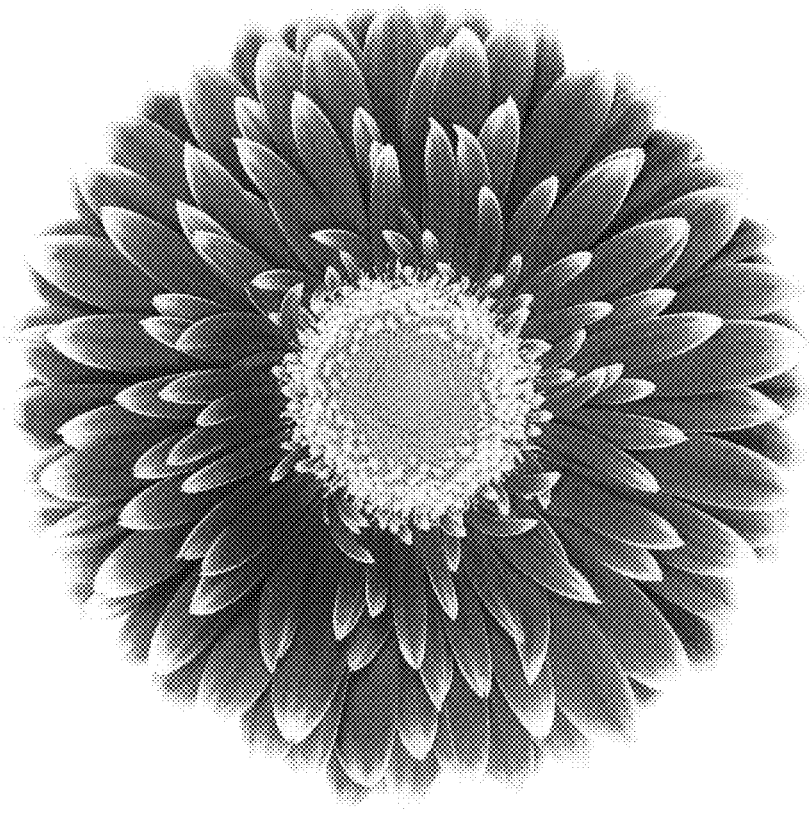

The photograph on the second sheet (FIG. 2) is a close-up view of a typical inflorescence of 'HILFHOTSPR'.

DETAILED BOTANICAL DESCRIPTION

The aforementioned photographs and following observations and measurements describe plants grown during the summer in 19-cm containers in a glass-covered greenhouse in De Kwakel, The Netherlands and under cultural practices typical of commercial garden *Gerbera* production. During the production of the plants, day temperatures ranged from 18° C. to 25° C. and night temperatures ranged from 15° C. to 18° C. Plants were six months old when the photographs were taken and nine months old when the description was taken. In the following description, color references are made to The Royal Horticultural Society Colour Chart, 2015 Edition, except where general terms of ordinary dictionary significance are used.

Botanical classification: *Gerbera hybrida* 'HILFHOTSPR'.

Parentage:

*Female, or seed, parent*.—Proprietary selection of *Gerbera hybrida* identified as code number 1679, not patented.

*Male, or pollen, parent*.—Proprietary selection of *Gerbera hybrida* identified as code number 1680, not patented.

Propagation:

*Type*.—By cuttings and in vitro meristem culture.

*Time to initiate roots, by cuttings, summer and winter*.—About 3.5 weeks at minimum temperatures of 20° C.

*Time to initiate roots, by tissue culture, summer and winter*.—About 2.5 to 3 weeks at minimum temperatures of 20° C.

*Time to produce a rooted young plant, by cuttings, summer and winter*.—About 3.5 weeks after rooting, at temperatures about 20° C. to 26° C.

*Time to produce a rooted young plant, by tissue culture, summer and winter*.—About five to six weeks at temperatures about 20° C. to 26° C.

*Root description*.—Fibrous; typically white in color, actual color of the roots is dependent on substrate composition, water quality, fertilizer type and formulation, substrate temperature and physiological age of roots.

Plant description:

*Appearance*.—Herbaceous perennial that is typically grown as a container or garden plant; compact, broadly upright and uniformly mounding; roughly flattened globular in shape; numerous leaves arranged in basal rosettes; dense and bushy habit; inflorescences held above the foliar plane on erect and strong basal peduncles; moderately vigorous to vigorous growth habit and moderate growth rate.

*Plant height, soil level to top of foliar plane*.—About 32.6 cm.

*Plant height, soil level to top of inflorescences*.—About 51.4 cm.

*Plant width or spread*.—About 60.5 cm.

Leaf description:

*Arrangement*.—Alternate, basal, simple.

*Length*.—About 30.4 cm.

*Width*.—About 17.3 cm.

*Shape*.—Ovate to elliptic in overall outline; runciate.

*Apex*.—Obtuse.

*Base*.—Hastate and short attenuate.

*Margin*.—Coarsely and irregularly angulate.

*Texture and luster, upper surface*.—Moderately pubescent; moderately glossy.

*Texture and luster, lower surface*.—Moderately to densely pubescent, slightly glossy.

*Venation pattern*.—Pinnate.

*Color*.—Developing leaves, upper surface: Close to 137B. Developing leaves, lower surface: Close to 147B. Fully expanded leaves, upper surface: Close to NN137A; venation, close to 147B. Fully expanded leaves, lower surface: Close to 144A; venation, close to 146B and 146C.

*Petioles*.—Length: About 8.1 cm. Diameter: About 6 mm. Texture and luster, upper and lower surfaces: Densely pubescent; slightly glossy. Strength: Moderately strong to strong. Color, upper surface: Close to 143A; towards the margins, close to 148A. Color, lower surface: Close to 146A to 146B.

Inflorescence description:

*Appearance*.—Composite inflorescence form with oblanceolate to narrowly oblanceolate-shaped ray florets; solitary inflorescences borne on upright and moderately strong peduncles and held above the foliar plane; ray and disc florets arranged acropetally on a capitulum; inflorescences face upright.

*Fragrance*.—None detected.

*Flowering season*.—Plants begin flowering about four months after planting; under garden conditions in The Netherlands, plants flower from spring to late autumn; plants can be flowered year-round in the greenhouse.

*Inflorescence longevity*.—Depending on the temperature, inflorescences last about three weeks on the plant; inflorescences persistent.

*Quantity of inflorescences*.—Freely flowering habit with at least six open inflorescences at one time.

*Inflorescence buds*.—Height: About 1.6 cm. Diameter: About 3 cm. Shape: Flattened hemispherical. Texture and luster: Densely pubescent; matte. Color: Close to NN137D; immature ray florets, close to N144D.

*Inflorescence size*.—Diameter: About 14 cm. Depth (height): About 3.8 cm. Diameter of disc: About 4.2 cm.

*Receptacles*.—Height: About 5 mm. Diameter: About 1.2 cm. Shape: Flattened globular. Color: Close to 157B.

*Ray florets*.—Quantity and arrangement: About 400 per inflorescence arranged in about ten whorls. Orientation: Proximally, about 60° from vertical; distally, close to horizontal to slightly downward. Length: About 5 cm. Width: About 1.1 cm. Shape: Oblanceolate to narrowly oblanceolate. Apex: Narrowly obtuse to broadly and bluntly acute. Base: Narrowly cuneate. Margin: Entire; not undulate. Texture and luster, upper surface: Smooth, glabrous; velvety; matte. Texture and luster, lower surface: Smooth, glabrous; slightly velvety; slightly carinate; slightly glossy. Color: When opening, upper surface: Close to a blend of 60B and 61B; towards the apical margins and apex, close to 155C. When opening, lower surface: Close to 63B and 63C; towards the apex, close to 155A. Fully opened, upper surface: Close to N57B; towards the apex, close to 157D; venation, similar to lamina colors; color does not change with subsequent development. Fully opened, lower surface: Close to N155C and N155D; towards the apex, close to 154D; proximal margins, close to 62B; venation, similar to lamina colors; color does not change with subsequent development.

*Disc florets*.—Quantity and arrangement: About 800 disc florets at center of the inflorescence arranged in about a ten-whorl spiral; lower 80% of the disc floret is fused. Length: About 1.8 cm. Width: About 5 mm. Shape: Tubular with one or two narrow free lobes and one broader free lobe. Apex: Acute and recurved. Base: Fused. Margin, free lobes: Entire; not undulate. Texture, upper surface: Smooth, glabrous; moderately velvety; matte. Texture, lower surface: Smooth, glabrous; slightly velvety; slightly glossy. Color: When opening, inner and outer surfaces: Close to 54B; towards the apex, close to 150D; mid-section and towards the base, close to 155D. Fully opened, inner surface: Close to 55A; towards the apex, close to 155A; mid-section and towards the base, close to NN155A. Fully opened, outer surface: Close to 55B; towards the apex, close to 155A; mid-section and towards the base, close to NN155A.

*Pappus*.—Quantity of hairs per floret: Numerous. Length: About 7 mm. Diameter: Fine, less than 1 mm. Texture and luster: Soft; matte. Color: Close to 161D.

*Phyllaries*.—Quantity and arrangement: About 80 per inflorescence arranged in about three whorls. Length: About 1.5 cm. Width (at base): About 3 mm. Shape: Narrowly lanceolate to narrowly oblanceolate. Apex: Narrowly acute. Base: Cuneate. Margin: Entire. Texture and luster, upper surface: Smooth, glabrous; moderately glossy. Texture and luster, lower surface: Moderately to densely pubescent; matte. Color, upper surface: Close to a blend of 143A and 144A. Color, lower surface: Close to 137B; towards the base, close to 137A.

*Peduncles*.—Length: About 45.9 cm. Diameter: Proximally, about 7 mm; distally, about 6 mm. Strength: Moderately strong. Angle: About 15° from vertical. Texture and luster: Densely pubescent; moderately glossy. Color: Close to 146A to 146B.

*Reproductive organs*.—Androecium (present on disc florets only): Quantity per floret: Five. Filament length: About 7 mm. Filament color: Close to 155C. Anther shape: Linear; basifixed. Anther size: About 4 mm by 0.3 mm. Anther color: Close to 14B. Pollen amount: Moderate. Pollen color: Close to 15A. Gynoecium (present on ray and disc florets): Quantity per floret: One. Pistil length: About 1.2 cm. Stigma diameter: About 0.3 mm. Stigma shape: Cleft. Stigma color: Close to 155A. Style length: About 1.15 cm. Style color: Close to N155B. Ovary color: Close to 157D.

*Seeds and fruits*.—To date, seed and fruit production has not been observed on plants of the new *Gerbera*.

Pathogen & pest resistance: To date, resistance to pathogens and pests common to *Gerbera* plants has not been observed on plants of the new *Gerbera* grown under commercial production conditions.

Garden performance: Plants of the new *Gerbera* have been observed to have good garden performance and to tolerate temperatures ranging from about −5° C. to about 35° C. and to be cold hardy to USDA Hardiness Zone 8.

It is claimed:

1. A new and distinct *Gerbera* plant named 'HILFHOT-SPR' as illustrated and described.

* * * * *